United States Patent [19]
Ueda et al.

[11] Patent Number: 4,805,618
[45] Date of Patent: Feb. 21, 1989

[54] OVIDUCT CLOSING APPARATUS

[75] Inventors: Yasuhiro Ueda; Isao Nagai; Naruto Shinkai; Masaaki Nakazawa; Toshiki Terayama, all of Tokyo, Japan

[73] Assignee: Olympus Optical Co., Ltd., Tokyo, Japan

[21] Appl. No.: 183,288

[22] Filed: Apr. 11, 1988

Related U.S. Application Data

[63] Continuation of Ser. No. 891,525, Jul. 31, 1986, abandoned.

[30] Foreign Application Priority Data

Aug. 8, 1985 [JP] Japan .................. 60-174701
Aug. 8, 1985 [JP] Japan .................. 60-174702
Aug. 8, 1985 [JP] Japan .................. 60-174703
Oct. 30, 1985 [JP] Japan .................. 60-243376

[51] Int. Cl.⁴ .................. A61B 17/08; A61B 17/00
[52] U.S. Cl. .................. 128/346; 128/325
[58] Field of Search .................. 128/334 R, 325, 346, 128/326, 130, 92 YN

[56] References Cited

U.S. PATENT DOCUMENTS

| | | | |
|---|---|---|---|
| 3,344,649 | 10/1967 | Wood | 128/340 |
| 3,805,767 | 4/1974 | Erb | 128/130 |
| 3,868,956 | 3/1975 | Alfidi et al. | 128/345 |
| 3,882,854 | 5/1975 | Hulka et al. | 128/6 |
| 3,915,761 | 10/1975 | Tschinkel et al. | 148/426 |
| 3,954,108 | 5/1976 | Davis | 128/325 |
| 4,170,990 | 10/1979 | Baumgart et al. | 128/92 YN |
| 4,198,081 | 4/1980 | Harrison et al. | 148/426 |
| 4,243,037 | 1/1981 | Smith | 128/303 R |
| 4,325,377 | 4/1982 | Boebel | 128/326 |
| 4,365,621 | 12/1982 | Brundin | 128/130 |
| 4,489,725 | 12/1984 | Casey et al. | 128/346 |
| 4,503,569 | 3/1985 | Dotter | 128/325 |
| 4,505,767 | 3/1985 | Quin | 420/441 |
| 4,509,504 | 4/1985 | Brundin | 128/346 |
| 4,512,338 | 4/1985 | Balko oet al. | 128/341 |
| 4,523,590 | 6/1985 | Roth et al. | 128/135 |
| 4,537,186 | 8/1985 | Verschoof et al. | 128/130 |
| 4,553,545 | 11/1985 | Maass | 128/341 |
| 4,580,563 | 4/1986 | Gross | 128/92 YC |
| 4,602,632 | 7/1986 | Jorgenson | 128/325 |
| 4,635,637 | 1/1987 | Schreiber | 128/337 |

FOREIGN PATENT DOCUMENTS 1113110 9/1984 U.S.S.R. .................. 128/92 YN

Primary Examiner—Richard C. Pinkham
Assistant Examiner—Gary Jackson
Attorney, Agent, or Firm—Frishauf, Holtz, Goodman & Woodward

[57] ABSTRACT

An oviduct-closing apparatus includes a body having a clamping portion. The clamping portion is prepared from a shape memory alloy. The clamping portion deforms into an open state engageable with an oviduct or a closed state capable of clamping the oviduct, in accordance with temperature change.

7 Claims, 5 Drawing Sheets

OVIDUCT CLOSING APPARATUS

This application is a continuation of application Ser. No. 891,525, filed July 31, 1986, now abandoned.

BACKGROUND OF THE INVENTION

This invention relates to an oviduct-closing apparatus for effecting contraception.

One of the contraceptive processes known to-date consists of cauterizing the oviduct. However, this process is accompanied with the drawbacks that great difficulties are encountered in the operation, the operator is demanded to have extremely advanced skills, and after operation the oviduct cannot be returned to normal functioning.

For the resolution of the above-mentioned difficulties, there have been proposed the process of closing the oviduct by means of a clip, and also the process of pouring silicone rubber into the oviduct and hardening the rubber in order to close the oviduct. However, these proposed processes are still hampered by the following difficulties. In the case of applying a clip, difficulties arise in fitting the clip to the oviduct and removing it therefrom, and moreover a large and complex device must be provided. When silicone rubber is used, a great deal of time is necessary before the silicone rubber is fully hardened, thus extending the operation and subjecting the patient to great pain. Moreover, a large and complex device has to be used to pour unhardened silicone rubber into the oviduct. Moreover, the silicone rubber process is hampered by the problem that when the silicone rubber is removed from the oviduct, the rubber tends to split at an interim portion, thus failing to attain the regeneration of the oviduct's function.

SUMMARY OF THE INVENTION

This invention has been accomplished in view of the above-mentioned circumstances and is intended to provide an oviduct-closing apparatus which dispenses with large and complex equipment and ensures the reliable closure and reopening of the oviduct.

To attain the above-mentioned object, according to one aspect of the present invention, there is provided an oviduct-closing apparatus which comprises: a body which is prepared from a shape memory alloy and has a clamp portion varied with temperature between an open state and an oviduct-clamping state.

According to another aspect of the present invention, there is provided an oviduct-closing apparatus which comprises: a body which is prepared from original shape-memory alloy and has its shape varied with temperature between a contracted state allowing for insertion into the oviduct and an expanded state ensuring a tight engagement in the oviduct.

BRIEF DESCRIPTION OF THE DRAWINGS

FIGS. 1 to 4 indicate an oviduct-closing apparatus according to a first embodiment of the present invention; in which FIG. 1 is a perspective view of the apparatus when left open, FIG. 2 is a side view of the apparatus when closed, FIG. 3 is a side view of the apparatus when held by a support, and FIG. 4 illustrates the manner in which the oviduct is tightly closed by the oviduct-closing apparatus;

FIGS. 8 to 11 represent the oviduct-closing apparatus according to a second embodiment; in which FIGS. 8 and 9 are perspective views of the apparatus when closed and opened, FIG. 10 is a view showing the apparatus engaged with the oviduct, and FIG. 11 is a view showing the oviduct tightly closed by the apparatus;

FIGS. 22 to 25 represent an oviduct-closing apparatus according to a third embodiment; in which FIGS. 22 and 23 are sectional views of the apparatus when contracted and expanded FIG. 24 is a view showing the apparatus inserted into the oviduct, and FIG. 25 is a view of the apparatus securely set in the oviduct;

FIGS. 27 to 30 indicate an oviduct-closing apparatus according to a fourth embodiment; in which FIGS. 27 and 28 are sectional views of the apparatus when contracted and expanded, FIG. 29 is a view showing the apparatus inserted into the oviduct, and FIG. 30 is a view showing the apparatus fixed in the oviduct.

DETAILED DESCRIPTION OF THE PREFERRED EMBODIMENTS

Description may now be made with reference to the accompanying drawings of an oviduct-closing apparatus embodying this invention.

Figure 1:
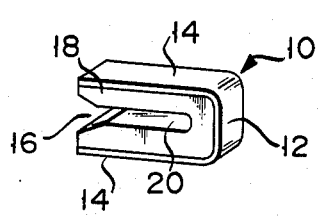

As seen from FIG. 1, an oviduct-closing apparatus comprises substantially U-shaped body 10 which is formed by bending a plate-like member. Body 10 is prepared from a unidirectional shape memory alloy, for example, a Ti-Ni alloy adaptable for a human. Body 10 has intermediate section 12 and a pair of parallel clamping strips 14 extending from both ends of intermediate section 12. Clamping strips 14 jointly constitute the later-described oviduct-clamping portion 16. The mutually facing insides of strips 14 and the inside of intermediate section 12 are coated with elastic layers 18 prepared, for example, from synthetic resin or rubber.

Figure 2:
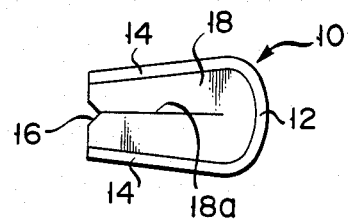

As shown in FIG. 2, clamping strips 14 of body 10 are so bent as to approach each other to cause elastic layers 18 to contact each other, that is, to cause the clamping portion 16 to close. In this state, the crystal structure of the shape memory alloy constituting body 10 indicates the matrix, namely, the basic form of body 10 is represented by its closed state. Thereafter, body 10 is cooled substantially to room temperature, and then, as shown in FIG. 1, deformed in an open state wherein clamping strips 14 are separated in parallel and gap 20 is defined between elastic layers 18 coated on the inner surfaces of the strips 14. When left in the open state, the shape memory alloy presents a martensitic phase. The temperature, at which the shape memory alloy constituting clamping portion 16 has its phase changed from the martensitic phase to the matrix, i.e., the transformation temperature of the alloy, is set to a level slightly higher than the body temperature, for example, 40° C. Therefore when body 10 is heated to a level higher than the transformation temperature, clamping portion 16 has its shape changed from the open to the closed state.

Figure 3:
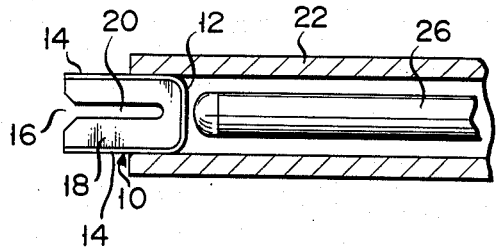
Figure 4:
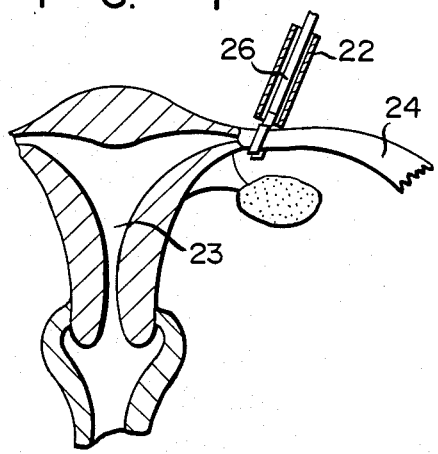

When the oviduct is closed by the oviduct-closing apparatus constructed as mentioned above, the undermentioned steps are taken. First, as shown in FIGS. 3 and 4, the apparatus is supported by support 22 formed of flexible pipe with the intermediate portion 12 of body 10 being inserted into the distal end of the support. The apparatus and support 22 are brought to the proximity of oviduct 24 of womb 23 through a laparoscope (not shown). As a result, oviduct 24 is engaged with gap 20, thereby causing clamping strips 16 to face both sides of oviduct 24. Under this condition, heating probe 26 is inserted into the coeliac cavity through support 22, causing body 10 of the oviduct-shutting apparatus to be heated to a higher temperature than the transformation temperature. Paired clamping strips 14 deform so as to approach each other, causing clamping portion 16 to be closed. Thus, oviduct 24 is closed by being clamped by elastic member 18 provided on the inner surfaces of clamping strips 14.

According to the oviduct-closing apparatus constructed as described above, clamping portion 16 deforms from the open state to the clamped state due to temperature change. Consequently the subject oviduct-closing apparatus can be fitted to the oviduct easily and reliably by means of a simple device, thereby ensuring the closure of the oviduct. Since elastic member 18 is provided on the inner surfaces of clamping strips 14, oviduct 24 can be reliably closed by the elastic member by slightly deforming the clamping strips. Therefore, the opening and closing of clamping portion 16 can be reliably carried out over a long period of time without giving rise to noticeable warpage in clamping strips 14 and intermediate section 12.

Figure 5:
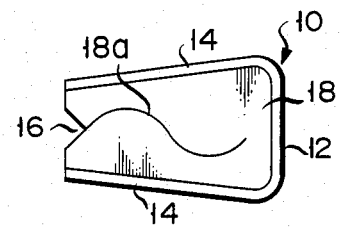
FIGS. 5 and 6 are side views respectively showing first and second modifications of the first embodiment.
Figure 6:
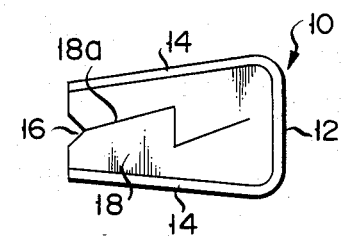

Contact surfaces 18a of the mutually facing elastic members 18 are formed flat (see FIG. 2). However, contact surfaces 18a may assume a waveform (FIG. 5) or saw teeth form (FIG. 6). Surfaces 18a illustrated in FIGS. 5 and 6 offer the advantage that when engaged with the oviduct in the open state, the oviduct-closing apparatus is less likely to disengage from the oviduct.

Figure 7:
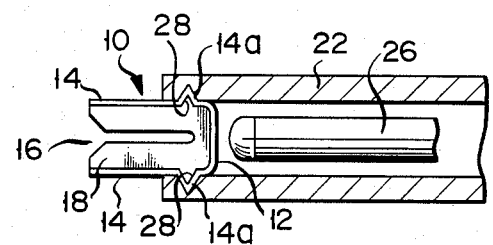
FIG. 7 is a cross sectional view showing a third modification of the first embodiment which is held by a support.

As illustrated in FIG. 7, clamping strips 14 may be provided with protuberances 14a. In this case, the inner wall of support 22 is provided with a pair of depressions 28 engageable with protuberances 14a. The oviduct-closing apparatus is engaged with support 22 with clamping portion 16 left open. When clamping portion 16 is closed by heating, protuberances 14a fall from depressions 28. The modification of FIG. 7 offers the advantage that the oviduct-closing apparatus is prevented from falling from support 22 before it is set on the oviduct.

Description may now be made with reference to FIGS. 8 to 11 of an oviduct-closing apparatus according to a second embodiment of this invention. Body 10 is formed by bending a wire consisting of a unidirectional shape memory alloy. Body 10 has U-shaped section 30 and a pair of parallel linear portions 32 extending along both sides of U-shaped section 30. Linear portions 32 are connected to section 30 by means of bent portions 34. Section 30 and paired linear portions 32 jointly constitute oviduct-clamping portion 16.

Figure 8:
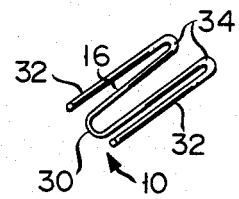
Figure 9:
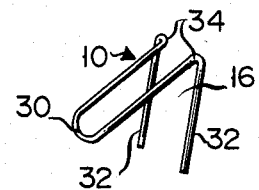

The closed state of FIG. 8 represents the basic form of body 10, and, as seen from FIG. 9, it is plastically deformed into a state in which clamping portion 16 is left open. When the shape memory alloy constituting body 10 is heated to a transformation temperature, for example, a higher level than 40° C., clamping portion 16 deforms from the open state to the closed state.

Figure 10:
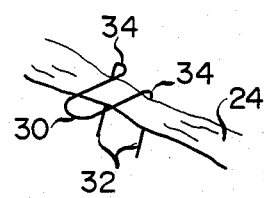
Figure 11:
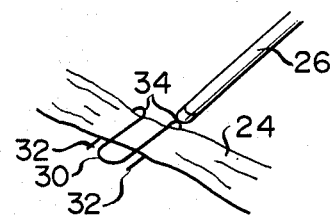

As illustrated in FIG. 10, the oviduct-closing apparatus is inserted into the coeliac cavity by means of a laparoscope (not shown) and supporting means with clamping portion 16 left open, and is engaged with oviduct 24. When oviduct-closing apparatus is heated to a higher level than the transformation temperature by heating probe 26, clamping portion 26 is closed. As a result, oviduct 24 is closed by being clamped by U-shaped section 30 and linear section 32.

Figure 12:
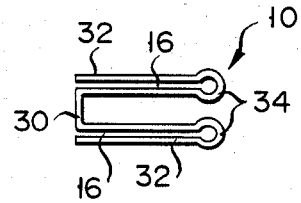
FIGS. 12 and 13 are respectively plan views of first and second modifications of the second embodiment.
Figure 13:
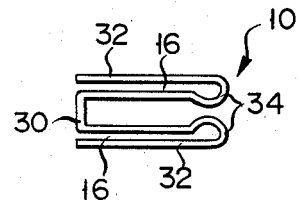

The oviduct-closing apparatus can shut the oviduct easily and reliably by means of a simple device. Referring to the second embodiment, bent portions 34 can be formed with a large curvature radius as shown in FIGS. 12 and 1. In this case, strains occurring in bent portions 34, as clamping section 16 is opened or closed, can be minimized.

Figure 14:
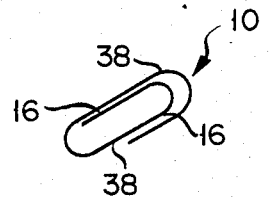
FIGS. 14 and 15 are perspective views of a third modification of the second embodiment, showing the closed and open states.
Figure 15:
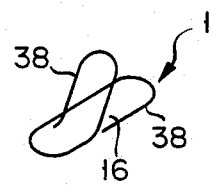

As set forth in FIGS. 14 and 15, body 10 may be formed in a clip shape having a pair of bent portions 38. The bent portions 38 jointly constitute oviduct-clamping portion 16. When oviduct-clamping portion 16 is opened, one of the portions 38 is erected as shown in FIG. 15.

Figure 16:
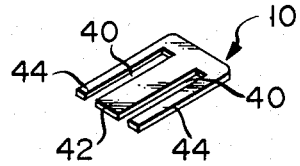
FIGS. 16 and 17 are perspective views of a fourth modification of the second embodiment, showing the closed and open states.
Figure 17:
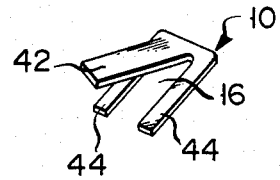

According to a third modification (FIGS. 16 and 17), body 10 is formed of a rectangular plate. A pair of parallel slits 40 are formed in the rectangular plate, thereby defining an intermediate portion 42 and a pair of side portions 44. Intermediate portion 42 and paired side portions 44 jointly constitute oviduct-clamping portion 16. Clamping portion 16 deforms in accordance with temperature change between the open state in which intermediate section 42 is raised and the closed state in which section 42 is thrown downward.

Figure 18:
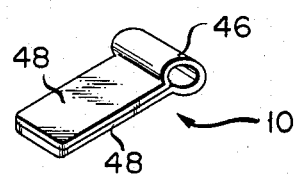
FIGS. 18 and 19 are perspective views of a fifth modification of the second embodiment, showing the closed and open states.
Figure 19:
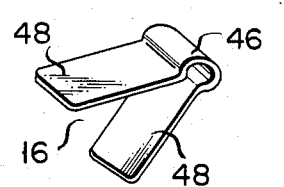

According to a modification shown in FIGS. 18 and 19, body 10 is made of a plate-like member and has bent portion 46 and a pair of mutually facing clamping strips 48 extending from bent portion 46. These clamping strips 48 collectively constitute oviduct-clamping portion 16.

Throughout the first and second embodiments, clamping portion 16 deforms from the open state to the closed state when body 10 is heated to a higher level than the transformation temperature. However, it is possible to cause clamping portion 16 to reversely deform from the closed state to the open state when body 10 is heated to a higher level than the transformation temperature. Further, body 10 may be prepared from two-directional shape memory alloy. In this case, the subject oviduct-closing apparatus can be adapted so that clamping portion 16 is closed when the temperature reaches a predetermined high level and is opened when the temperature drops to a predetermined low level, or clamping portion 16 is closed when the temperature falls to a predetermined low level and is opened when the temperature is raised to a prescribed high level.

Moreover, body 10 can have its transformation temperature set at substantially the same level as the body temperature. In this case, body 10 may deform at the body temperature without any extra means such as a heating probe. Further, it is possible to cover the surface of body 10 with a soft substance such as Teflon, thereby preventing the internal organs such as the oviduct from being damaged by the oviduct-closing apparatus.

Figure 20:
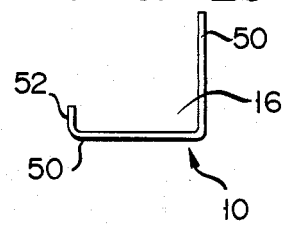
FIGS. 20 and 21 are side views of a sixth modification of the second embodiment, showing the open and closed states.
Figure 21:
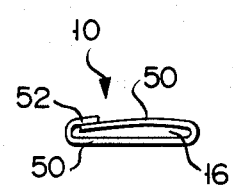
Figure 22:
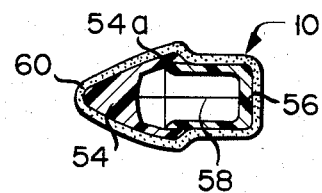

Referring to a modification of FIGS. 20 and 21, body 10 is formed of a substantially L-shaped plate. Body 10 has a pair of clamping strips 50 intersecting each other at right angles and defining clamping portion 16. The free end of one of clamping strips 50 is bent to provide holding portion 52. When the oviduct-closing apparatus is fitted to oviduct 24, clamping portion 16 is closed to the state of FIG. 21 by proper means. When body 10 is heated to a higher level than the transformation temperature, clamping portion 16 shown in FIG. 20.

Description may now be made with reference to FIGS. 22 to 25 of an oviduct-closing apparatus according to a third embodiment of the invention. Body 10 of the apparatus includes substantially conical component 54 open at the bottom and cylindrical pushing component 56 having a bottom. The open end of component 56 is engaged with the inner bottom end of component 54. Conical component 54 is prepared from, for example, synthetic resin, the peripheral wall 54a of the bottom portion can be deformed radially outward. Pushing component 56 is prepared from harder elastic material than deformable conical component 54, and is connected to component 54 by wire-like drive member 58 prepared from a unidirectional shape memory alloy. The surface of conical component 54 and pushing component 56 are coated with elastic layer 60.

Figure 23:
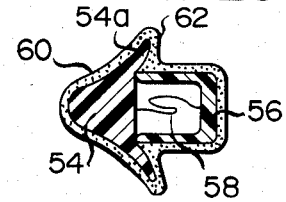

Drive member 58 is worked to present a basic bent form shown in FIG. 23. In this state, the crystal structure of the shape memory alloy constituting drive member 58 indicates the matrix. The drive member 58 is cooled to a level approaching room temperature and plastically deformed in a straight line. Under this condition, the shape memory alloy indicates a martensitic phase. The transformation temperature of the alloy constituting the drive member 58, at which the alloy deforms from the linear form to the bent form, is defined to be a level slightly higher than the body temperature, that is, 40° C. When the oviduct-closing apparatus is heated to a higher level than the transformation temperature, the drive member 58 deforms from the linear to the curved state. Thus, pushing member 56 is pulled toward conical member 54 by drive member 58. Accordingly, the peripheral wall 54a of conical member 54 is pushed by the distal end of member 56 to be expanded radially outward. The resultant deformed peripheral wall 54a constitutes protuberance 62.

Figure 24:
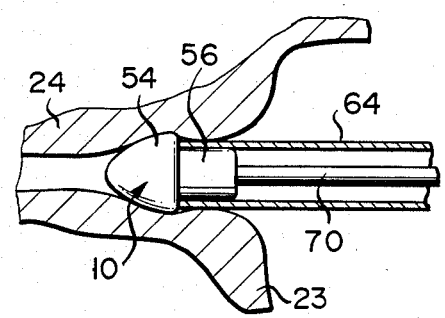
Figure 25:
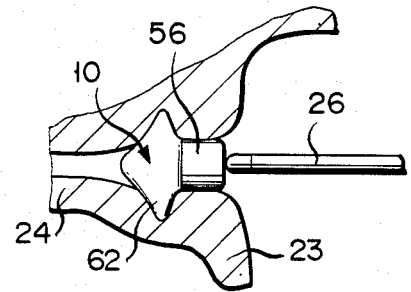

When the oviduct is closed by the oviduct-closing apparatus constructed as described above, the undermentioned steps are taken. First, as shown in FIG. 24, the distal end of cylindrical component 56 is inserted into the distal end of a guide tube 64. The apparatus is inserted into womb 23 by means of guide tube 64 and an endoscope, and is pressed against the inlet of oviduct 24. Pressure rod 70 is inserted into guide tube 64, causing the oviduct-closing apparatus to be pushed into oviduct 24. As shown in FIG. 25, heating probe 26 is inserted in place of guide tube 64 into womb 23 by means of an endoscope to heat the oviduct-closing apparatus. When the apparatus is heated to a higher level than the transformation temperature, drive member 58 deforms from the linear state to the bent contracted state. As a result, push member 56 is pulled toward conical member 54, whose peripheral wall 54a is forced outward to provide protuberance 62, which in turn bulges oviduct 24. Thus, the oviduct-closing apparatus is held in the oviduct while reliably closing it.

When the oviduct-closing apparatus is drawn away from oviduct 24, it is advised to grip the apparatus by means of a handling instrument such as forceps taken into the womb trough an endoscope.

The oviduct-closing apparatus constructed as described above offers the advantages that the oviduct can be reliably closed easily by heating the drive member, dispensing with any large and complex instruments and what is better, facilitating the possible reopening of the oviduct.

Figure 26:
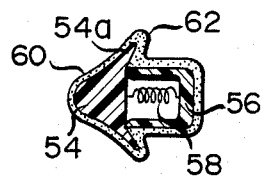
FIG. 26 is a sectional view of a modification of the third embodiment.

Referring to the third embodiment, the basic form of drive member 58 may assume the coiled form as illustrated in FIG. 26, and further may be prepared from 2-directional shape memory alloy. In this case, the drive member can be contracted by being heated to a predetermined high level temperature and extended by being cooled to a predetermined low level temperature. Conversely, drive member 58 can be contracted by being cooled to a predetermined low level temperature and extended by being heated to a predetermined high level temperature. Therefore, the closure of the oviduct by the oviduct-closing apparatus and the reopening of the oviduct can be more facilitated. Further, the transformation temperature of the shape memory alloy constituting drive member 58 may be set at substantially the same level as the body temperature. In this case, drive member 58 can be deformed only by the body temperature without applying any extra heating means.

Figure 27:
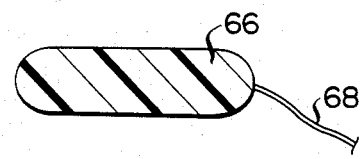
Figure 28:
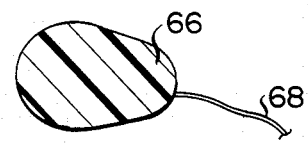

Description may now be made with reference to FIGS. 27 to 30 of an oviduct-closing apparatus according to a fourth embodiment of the present invention. As shown in FIG. 27, the oviduct-closing apparatus comprises a deformable member 66 prepared from shape memory polymer and drawable cord 68 embedded at one end in deformable member 66. The shape memory polymer has such a nature that it indicates elasticity like that of rubber at a higher level than the glass transition temperature (Tg), and is hardened like plastics material when cooled to a lower level than the glass transition temperature. The shape memory polymer is prepared from a polymer of norbornane series, and the glass transition temperature is set at 40° to 45° C. While heated to a higher level than the glass transition temperature, deformable member 66 is formed into the shape of a rod having a sufficiently small diameter to be inserted into the oviduct (FIG. 27), and later cooled to a lower level than the glass transition temperature to retain the illustrated state. When heated to a higher level than the glass transition temperature, namely, over 40° C., deformable member 66 has its diameter increased to assume an expanded form (FIG. 28).

Figure 29:
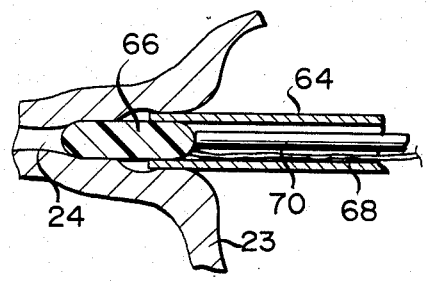
Figure 30:
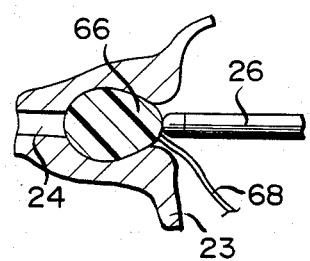

When the oviduct-closing apparatus constructed as mentioned above is used to close the oviduct, the undermentioned steps are taken. First, as shown in FIG. 29, deformable member 66 is held at the distal end of guide tube 64, and inserted in this state into womb 23 through an endoscope. The distal end of member 66 is pressed against the inlet of oviduct 24. Then, pressure rod 70 is inserted into guide tube 64, and the apparatus is pushed into oviduct 24 by the rod. Later, heating probe 26 is taken into womb 23 in place of guide tube 64. Deformable member 66 is heated by probe 26. When heated to a higher level than the glass transition temperature, deformable member 66 expands, thereby bulging oviduct 24. As a result, the oviduct-closing apparatus is tightly fitted into oviduct 24 to ensure its reliable closure.

When it is desired to reopen oviduct 24, the oviduct-closing apparatus is drawn away from oviduct 24 by pulling cord 68 outward. Otherwise, it is possible to pull the apparatus out of oviduct 24 by a handling instrument such as forceps.

The oviduct-closing apparatus according to the fourth embodiment constructed as described above ensures the easy and reliable closing and reopening of the oviduct without applying any large and complex device, as in the preceding embodiments. In this connection it is to be noted that the heating of deformable member 66 may be effected not only by a heating probe, but also by conducting hot water through guide tube 64.

Figure 31:
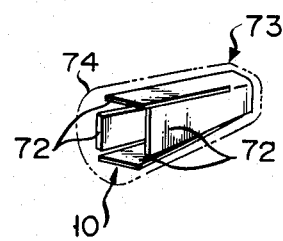
FIGS. 31 and 32 are perspective views of an oviduct-closing apparatus according to a fifth embodiment of this invention when closed and opened.
Figure 32:
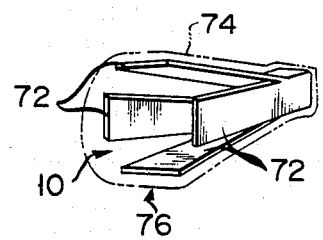

Description may now be made with reference to FIGS. 31 and 32 of an oviduct-closing apparatus according to a fifth embodiment of this invention. As seen from FIG. 31, body 10 of the apparatus includes deformable member 73 formed of four movable plates 72 joined together at one end so as to present the shape of a petal. Each plate 72 is prepared from shape memory alloy. Deformable member 73 is covered with elastic membrane 74. FIG. 31 shows the basic form of body 10 in which the free ends of the respective movable plates 72 are closed together. When heated to a higher level than the transformation temperature, body 10 has its movable plates 72 bent outward at the free end to present a larger diameter form. The outward bent free end portions of movable plates 72 jointly constitute protuberance 76. When, therefore, the closed oviduct-closing apparatus 10 is heated to a higher level than its transformation temperature after being inserted into the oviduct, movable plates 72 deform to close the oviduct.

Movable plates 72 may be prepared from 2-directional shape memory alloy as in the aforementioned first to third embodiments. The number of movable plates 72 need not be limited to four, but may be increased or decreased as need arises.

What is claimed is:

1. An oviduct-closing apparatus for closing an oviduct passage comprising:
a body provided with a passage closing portion which is deformable to assume an open state for engagement with an oviduct, and a closed state capable of closing the oviduct passage, said portion being prepared from a shape memory alloy and deforming from the open to the closed state or vice versa according to a predetermined temperature change;
a flexible support pipe means adapted to accommodate in its distal end at least a portion of said body;
a probe means sized to slide through said pipe means toward said distal end, and adapted to be heated to a preselected temperature;
wherein said body is constructed and arranged so that all of said body including said passage closing portion can be operatively applied to an oviduct when said body is inserted in the distal end of said flexible support pipe means, and the state of said passage closing portion is deformed by thermal contact with said probe means inserted into the support pipe means.

2. The apparatus according to claim 1, wherein said body is formed of plate-like shape memory alloy, and has an intermediate section and paired mutually facing clamping strips extending from the intermediate section; and said clamping strips are formed to be deformable between an open state in which said strips are separated from each other at the predetermined distance and a closed state in which said strips are drawn close to each other, thereby constituting said passage closing portion.

3. The apparatus according to claim 2, wherein said body is prepared from a unidirectional shape memory alloy having a predetermined transformation temperature so that when the body is heated to a higher level than the transformation temperature, said passage closing portion deforms from the open state to the closed state.

4. The apparatus according to claim 2, wherein said body is prepared from a unidirectional shape memory alloy having a predetermined transformation temperature so that when the body is heated to a higher level than the transformation temperature, said passage closing portion deforms from the closed state to the open state.

5. The apparatus according to claim 2, wherein said body is prepared from a 2-directional shape memory alloy having a high transformation temperature and a low transformation temperature so that when the body is heated to a higher level than that of the high transformation temperature, the passage closing portion deforms from the closed state to the open state and when the body is cooled to a lower level than that of the low transformation temperature, the clamping portion deforms from the closed state to the open state.

6. The apparatus according to claim 2, wherein said body is prepared from a 2-directional shape memory alloy having a high transformation temperature and a low transformation temperature so that when the body is heated to a higher level than that of the high transformation temperature, the passage closing portion deforms from the open state to the closed state and when the body is cooled a lower level than that of the low transformation temperature, the clamping portion deforms from the-open state to the closed state.

7. The apparatus according to claim 1, wherein said shape memory alloy is prepared from Ti-Ni alloy.

* * * * *